United States Patent [19]
Kendall

[11] Patent Number: 5,415,716
[45] Date of Patent: May 16, 1995

[54] APPARATUS FOR SYNCHRONOUS IN-LINE PLACEMENT OF ABSORBENT PANEL COMPONENT

[75] Inventor: Jeffrey D. Kendall, Kent, Wash.

[73] Assignee: Paragon Trade Brands, Inc., Federal Way, Wash.

[21] Appl. No.: 57,440

[22] Filed: May 4, 1993

Related U.S. Application Data

[63] Continuation of Ser. No. 854,354, Mar. 19, 1992, abandoned.

[51] Int. Cl.⁶ ............................................. B32B 31/00
[52] U.S. Cl. ..................................... 156/256; 156/362; 156/364; 156/540; 156/541; 156/542
[58] Field of Search ............... 156/362, 363, 364, 542, 156/541, 540, 256

[56] References Cited

U.S. PATENT DOCUMENTS

| | | | |
|---|---|---|---|
| 2,641,416 | 6/1953 | McCleary et al. | 156/361 X |
| 2,895,534 | 7/1959 | Steidinger | 156/552 X |
| 3,446,451 | 5/1969 | Wilcox | 242/75.43 |
| 3,860,002 | 1/1975 | Kolbach . | |
| 3,957,570 | 5/1976 | Helum | 156/519 |
| 4,171,239 | 10/1979 | Hirsch et al. . | |
| 4,297,157 | 10/1981 | Van Vilet . | |
| 4,364,787 | 12/1982 | Radzins . | |
| 4,585,506 | 4/1986 | Matsuguchi | 156/361 |
| 4,642,150 | 2/1987 | Stemmler . | |
| 4,680,080 | 7/1987 | Instance | 156/363 |
| 4,728,385 | 3/1988 | Hell | 156/353 |
| 4,735,673 | 4/1988 | Piron . | |
| 4,795,510 | 1/1989 | Wittrock et al. . | |
| 4,925,520 | 5/1990 | Beaudoin et al. . | |
| 5,045,135 | 9/1991 | Meissner | 156/64 |

Primary Examiner—W. Gary Jones
Assistant Examiner—Mark DeSimone
Attorney, Agent, or Firm—Dressler, Goldsmith, Shore & Milnamow, Ltd.

[57] ABSTRACT

An apparatus for effecting synchronous, in-line placement of pads of material, such as a highly absorbent compressed composite laminate, includes a supply reel for supplying a continuous web of material. The web of material is guided to a pair of pull rolls which effect movement of the web at a first velocity $V_1$. A cutting mechanism, preferably comprising cooperating knife and anvil rolls, cuts individual discrete pads of the material for presentation to an associated vacuum transfer drum. The vacuum transfer drum includes a peripheral surface operated at a second velocity $V_2$ equal to or greater than the first velocity $V_1$, with the velocity $V_2$ equal to the linear speed of movement of an associated continuous substrate, such as comprising air laid comminuted wood pulp. The discrete pads of material are thereby transferred onto the substrate at a relative spacing S between adjacent ones of the discrete pads, which spacing equals $L(V_2-V_1)-L$.

5 Claims, 2 Drawing Sheets

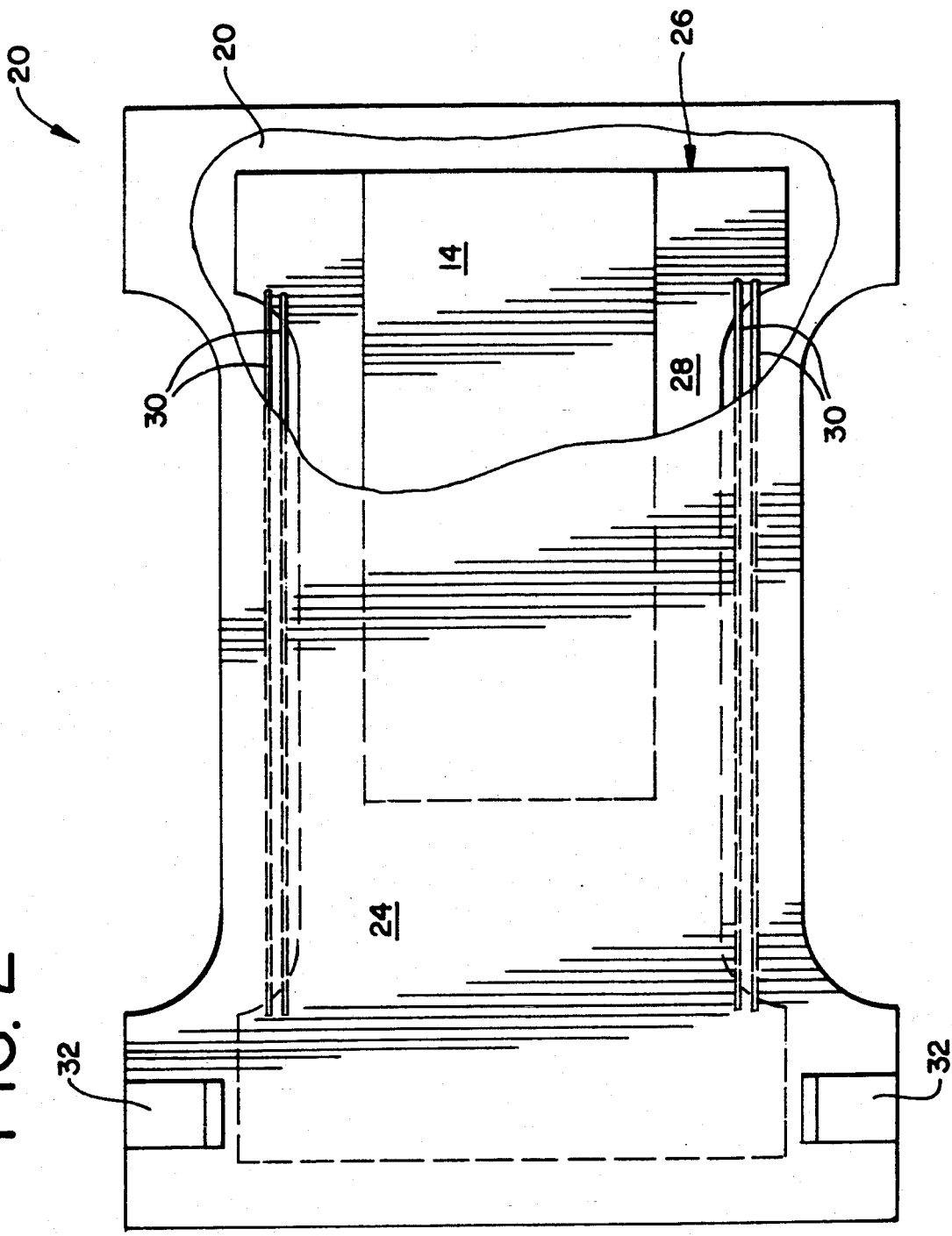

APPARATUS FOR SYNCHRONOUS IN-LINE PLACEMENT OF ABSORBENT PANEL COMPONENT

This application is a continuation of application Ser. No. 07/854,354, filed Mar. 19, 1992, abandoned.

TECHNICAL FIELD

The present invention relates generally to the manufacture of absorbent panel assemblies such as for use in disposable diapers, incontinent products, and the like, and more particularly to an apparatus for effecting selective, synchronous in-line placement of a discrete pad of absorbent material, or other component, onto a moving substrate for subsequent formation of discrete absorbent panel assemblies.

BACKGROUND OF THE INVENTION

Disposable absorbent products, such as disposable diapers and incontinent devices, have become increasingly sophisticated in recent years in an effort to enhance the absorptive and containment characteristics of such products. Products of this nature include an absorbent panel assembly which, in a simple form, typically comprises a batt or panel of comminuted wood pulp, sometimes referred to as wood fluff. In more sophisticated arrangements, superabsorbent polymeric material can be incorporated in the absorbent panel, with layered, or otherwise selectively thickened constructions further promoting efficient use of materials and effective absorption.

One particularly sophisticated and effective absorbent panel construction is disclosed in U.S. Pat. No. 4,500,315, to Pieniak et al. The absorbent material disclosed in this patent comprises a compressed composite laminate of a resilient fibrous web impregnated with in situ polymerized superabsorbent material. One or both sides of the compressed resilient web is provided with a densified layer of comminuted wood pulp, which layer functions to promote wicking and distribution of liquid to all portions of the assembly for efficient use of the superabsorbent material.

While the above-described compressed composite laminate has been found to exhibit superior absorptive and containment characteristics, it will be appreciated that its sophisticated nature results in such a construction being more costly than relatively simple wood pulp absorbent panel arrangements. However, studies have shown that the absorbent panel of a diaper or incontinent product is not usually subjected to uniform wetting, but rather, is subjected to generally localized wetting in a predictable fashion. As such, not all regions of an absorbent panel assembly need exhibit the superior performance characteristics which can be achieved with the above-described compressed composite laminate absorbent material.

Accordingly, the present invention contemplates a method and apparatus for manufacture of an absorbent panel assembly which permits selective placement of a discrete pad of material, such as comprising the above-described compressed composite laminate, in association with a larger absorbent panel which may comprise a less expensive material. In this way, an absorbent panel assembly can be provided with superior absorptive and containment characteristics in a cost-effective manner.

SUMMARY OF THE INVENTION

In accordance with the present invention, an apparatus and method are disclosed for effecting synchronous, in-line placement of discrete pads of material on a moving substrate for subsequent formation of discrete absorbent panel assemblies. The illustrated apparatus facilitates versatile and cost-effective placement of the discrete pads of material, which may comprise a highly absorbent composition if desired, and permits application of such discrete pads in a continuous manner so that the present apparatus can readily be incorporated in a continuously operable system for manufacture of disposable diapers, incontinent devices, or like absorbent products.

In accordance with the illustrated embodiment, the present apparatus includes an arrangement for supplying a continuous web of the pad material, which in the illustrated form comprises a power-driven supply reel of the pad material, and a pair of driven pull rolls which are operable to move the pad material. In this regard, selectively operable controls for the apparatus are operatively connected with the pull rolls so that the pad material is moved at a first velocity $V_1$.

In the preferred form, a tension sensing mechanism is provided downstream of the supply reel, but upstream of the pull rolls. In this manner, the tension of the continuous web of material is sensed and monitored as it moves from the supply reel to the pull rolls. The tension sensing mechanism is in turn operably connected to the drive for the supply reel so that the speed at which the supply reel is driven can be adjusted, thereby adjusting the tension of the continuous web of material.

In order to form the desired discrete pads of material from the continuous web, the present apparatus includes a cutting mechanism which receives the pad material from the pull rolls, and which cuts the pad material into the desired discrete pads, each having a length L. In the presently preferred form, the cutting mechanism comprises cooperating knife and anvil rolls of the so-called progressive compression type.

Immediately downstream of and adjacent to the cutting mechanism is an arrangement for transferring the discrete pads of the material in the desired synchronous manner onto the associated moving substrate. It is presently contemplated that the moving substrate comprises a continuous air laid web of absorbent material such a comminuted wood pulp. However, as will be recognized by those skilled in the art, the principles of the present invention can be readily employed for synchronously placing a wide variety of different discrete pads of material onto associated moving substrates comprising other than wood pulp.

In order to effect the desired synchronous placement of the discrete pads, the transfer mechanism, comprising a vacuum transfer drum in the illustrated embodiment, is operable to provide a peripheral surface of the drum with a second velocity $V_2$ equal to the linear speed of movement of the associated substrate. The second velocity $V_2$ is equal to, or preferably greater than, the first velocity $V_1$. The velocity $V_2$ is equal to the linear speed of movement of the associated substrate. By this arrangement, the spacing S between adjacent ones of the discrete pads on the moving substrate can be selectively varied, and equals $L(V_2/V_1)-L$.

Other features of the present invention facilitate selective placement of the discrete pads of material on the associated substrate in the desired manner. In the illustrated form, a pair of edge guide rolls are provided about which the continuous web of material is guided, with these guide rolls being selectively movable for laterally guiding the placement of the discrete pads relative to the centerline of the moving substrate. In the illustrated form, a substrate cutter is provided, such as in the form of a water knife assembly, for cutting the substrate into discrete panels each having a respective one of the discrete pads associated therewith. In the presently contemplated form, each discrete pad is shorter in length than its associated panel, with each pad preferably aligned with an end edge of the respective panel.

Other features and advantages of the present invention will become readily apparent from the following detailed description, the accompanying drawings, and the appended claims.

BRIEF DESCRIPTION OF THE DRAWINGS

FIG. 2 is a top plan view of a disposable diaper including an absorbent panel assembly formed through use of the present apparatus and method.

DETAILED DESCRIPTION

Figure 1:
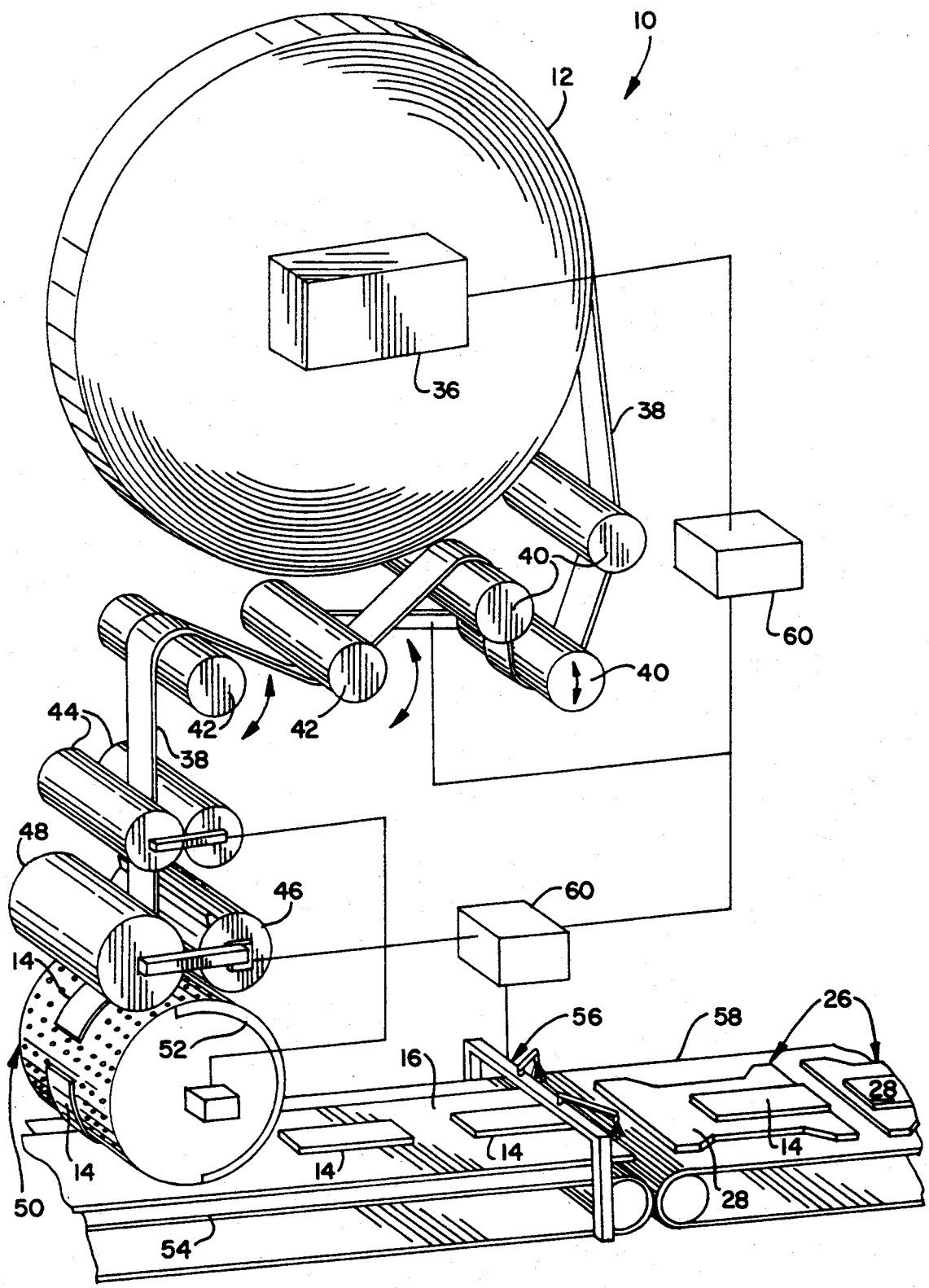
FIG. 1 is a diagrammatic view of an apparatus embodying the principles of the present invention for effecting synchronous in-line application of discrete pads of material to an associated moving substrate.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawings, FIG. 1 diagrammatically illustrates an apparatus 10 embodying the principles of the present invention for applying discrete pads of material to an associated moving substrate. It is presently contemplated that the present apparatus be employed for manufacture of discrete absorbent panel assemblies such as for use in disposable diapers, incontinent devices, and like absorbent products. However, it will be recognized that the principles disclosed herein can readily be employed for effecting placement of discrete pads of other than absorbent material in desired synchronous placement with an associated moving substrate.

It is presently contemplated that a supply reel 12 be employed from which discrete pads of material 14 are cut, for subsequent placement on associated moving substrate 16. It is presently preferred that each of the discrete pads 14 comprise a highly absorbent compressed composite laminate such as disclosed in U.S. Pat. No. 4,500,315, to Pieniak et al. However, other types of absorbent material can be employed. In contrast, it is contemplated that the moving substrate 16 may comprise a relatively less expensive and less sophisticated absorbent material, such as an air laid continuous batt of comminuted wood pulp.

With reference to FIG. 2, a relatively simplified form of disposable diaper 20 is illustrated, which diaper incorporates an absorbent panel assembly formed through use of the present invention. In accordance with the typical arrangement of such an absorbent product, disposable diaper 20 includes a liquid impermeable backsheet 22, and a generally coextensive liquid pervious topsheet 24, illustrated partially cutaway in FIG. 2.

Interposed between the backsheet 22 and the topsheet 24 in sandwich-like relationship therewith is an absorbent panel assembly 26. Absorbent panel assembly 26 is illustrated in a typical I-shaped or contoured configuration, and includes a discrete absorbent panel 28, such as comprising comminuted wood pulp, to the upper surface of which has been applied a discrete absorbent pad 14 formed in accordance with the present invention. While not illustrated, the absorbent panel assembly 26 further typically includes a tissue overwrap which substantially surrounds the juxtaposed absorbent panel 28 and discrete pad While the illustrated embodiment shows the discrete pad 14 arranged on the upper surface of the absorbent panel 28, it will be understood that such an orientation is for purposes of illustration only, and that the pad 14 can easily be arranged beneath the associated absorbent panel 28. As will also be recognized by those familiar with the art, the present method and apparatus can be employed for fabricating an absorbent panel assembly wherein the discrete pad 14 is interposed between a pair of the absorbent panels 28.

As illustrated, the discrete pad 14 is arranged at the forward portion of the diaper 20, and is aligned with the front end edge of the associated absorbent panel 28. Again, this can be selectively varied in accordance with the teachings herein. Studies have shown that this front portion of a disposable diaper is the region in which most liquid is received, and thus this region should desirably exhibit the most absorptive capacity. However, it is within the purview of the present invention to form the discrete pad 14 so as to extend substantially the full length of the associated absorbent panel 28, or to otherwise position the discrete pad 14, such as centrally, or rearwardly, with respect to the absorbent panel.

In accordance with the typical disposable diaper construction, diaper 20 preferably includes one or more longitudinally extending leg elastic elements 30 at each respective transverse or side edge of the construction, and a pair of pressure-sensitive tape tabs 32 respectively positioned at each of the rearward, ear portions of the diaper construction.

With reference again to FIG. 1, features and operations of the present apparatus will now be described.

The supply reel 12 carrying the material from which the discrete pads 14 are to be formed is provided with a suitable reel drive 36, with a continuous web 38 of the pad material thus being supplied. The continuous web 38 is unwound from the supply reel, and is guided about a plurality of dancer rollers 40 for effecting sensing and monitoring of the tension of the continuous web of material. In particular, a central or intermediate one of the dancer rolls 40, is relatively movable (note the double-headed arrow illustrated thereon), with this roller in turn operatively connected with a suitable feedback mechanism so that the tension of the continuous web of material can be monitored. The signal from the tension sensing device is in turn provided to the controls of the system, whereby the reel drive 36 for the supply reel 12 can be adjusted, thereby adjusting the tension of the continuous web.

Downstream of the dancer rolls 40 are a pair of cooperating edge guide rolls 42 about and between which the web of material 38 is guided. As will be recognized by those familiar with the art, edge guide rolls 42 are moved in tandem relationship so that their respective rotational axes are maintained in a constant, parallel relationship. However, the edge guide rolls 42 are movable together in a generally lateral, rocking-like motion, whereby the lateral or cross-wise position of the continuous web 38, and thus the discrete pads 14, relative to the centerline of substrate 16 can be selectively varied. While it is ordinarily contemplated that the discrete pads 14 will be arranged in a substantially centered relationship on the substrate 16 along its centerline, it will be appreciated that the provision of the edge guide rolls facilitates this desired placement, as well as any necessary adjustment thereof.

Downstream of the edge guide rolls, the continuous web 38 is fed between a pair of pull rolls 44. The driven pull rolls 44 serve a dual function. First, the pull rolls serve as a pinch point to handle the continuous web 38, and thereby primarily function as the first web velocity control point for subsequent supply of the web to the cutting mechanism of the present apparatus. In particular, the pull rolls are operated to move the continuous web of pad material at a first velocity $V_1$.

The pull rolls 42 further function to provide each discrete pad 14 with the desired length L. In particular, the pull rolls 42 are driven at a speed to provide a continuously variable ratio of one-to-one or less, relative to the linear speed of movement or surface velocity of the substrate web 16. The variable ratio establishes the length L of each discrete pad 14, with it presently preferred that the variable ratio be set at less than one-to-one so that the discrete pads 14 are spaced from each other by a spacing S on the substrate 16, thereby resulting in a final panel assembly wherein each discrete pad 14 extends less than the full length of its respective absorbent panel 28.

As noted, the pull rolls 44 establish the velocity $V_1$ of the web 38, with the web 38 thereafter being presented to a cutting mechanism of the present apparatus. In the illustrated embodiment, the cutting mechanism comprises cooperating knife and anvil rolls 46 and 48, which may be of the progressive compression type, or which may alternately be configured as a straight compression type or sheer type knife.

At the knife and anvil rolls, the web of material 38 is cut at a 90° angle relative to its length across the width of the web, thereby forming the discrete pads 14. It should be noted that synchronization of the knife is a very important aspect of the present apparatus, and is effected such that the knife motor is synchronized on a one-to-one angular basis with the pitch of the product, wherein the pitch is defined as distance from the leading edge of one pad assembly to the leading edge of the next pad assembly, prior to separation and spacing of the assemblies. In other words, the knife is operated such that a cut is effected in synchronization with each single one of the absorbent panel assemblies 26 to be ultimately formed. Notably, the synchronizing process for the knife is continuously variable, thus allowing the discrete pad 14 to be consistently placed anywhere along the substrate 16, thereby permitting disposition of the discrete pad 14 in a desired lengthwise position relative to the associated absorbent panel 28.

In order to place the individual discrete pads 14 on the moving substrate 16, the present apparatus 10 includes a transfer mechanism, which in the illustrated embodiment comprises a rotatable vacuum transfer drum 50. The transfer drum includes a rotatable, foraminous peripheral surface for applying vacuum to the discrete pads of material 14 for effecting transfer thereof from the cutting mechanism of the apparatus onto the moving substrate 16. This is achieved by moving the peripheral surface of the drum at a second velocity $V_2$ equal to or greater than the first velocity $V_1$, with the velocity $V_2$ equal to the linear speed of movement of the substrate 16. When the transfer drum is operated in this synchronized manner with the remainder of the apparatus, the spacing S between adjacent ones of the discrete pads 14 on the substrate 16 equals $L(V_2/V_1)-L$.

While other types of transfer mechanisms may alternately be employed, such as a vacuum transfer table or vacuum transfer belt, the principles of operation are essentially the same as for operating the vacuum transfer drum 50. As noted, the surface velocity of the drum is carefully maintained at a one-to-one relationship with respect to the surface velocity of the substrate 16. In order to effect transfer, the web of material 38 contacts the peripheral surface of the drum with the pad 14 which is being cut slipping on the surface of the vacuum drum prior to the actual completion of the cut and separation of the pad 14 from the web 38. As will be appreciated, the slippage results from the fact that the drum is preferably operated at a velocity $V_2$ greater than velocity $V_1$, although if it is desired to provide pads 16 so that there is no spacing therebetween, the second velocity $V_2$ can be equal to the first velocity $V_1$.

As the pad is cut from the web 38, the free edge of the pad is maintained in contact with the peripheral surface of the drum under the influence of the vacuum applied thereto. Once the pad 14 is cut to length by the cutting mechanism, the transfer drum 50 accelerates the pad up to the drum velocity, and then places it on the substrate 16 moving therebeneath. In a current embodiment, the transfer drum is ported for vacuum between 110° and 270° counterclockwise, such as by a suitable vacuum blocking mechanism 52 diagrammatically illustrated in FIG. 1. Typically, the vacuum drum operates at 18–25 inches of vacuum, with ten one-eighth inch holes centered across the face of the drum every ten degrees around the circumference thereof. Thus, each pad 14 is received by the drum, rotated about its surface for approximately 160°, and then deposited and transferred to the moving substrate 16.

As noted, the substrate 16 typically comprises an air laid continuous batt or web of comminuted wood pulp, and is supported and moved by a suitable conveyor 54. After each of the discrete pads 14 is transferred to the substrate 16, formation of the individual absorbent panel assemblies 26 is preferably effected. To this end, a substrate cutter 56 is preferably provided, such as in the form of a water knife assembly. If a tissue overwrap is to be applied to the substrate and discrete panel 14, it can be desirable to apply such a tissue overwrap upstream of the substrate cutter 56.

The substrate cutter cuts the substrate into discrete panels 28, which can be contoured, with each respective one of the pads 14 respectively associated with the panels 28. While it is presently preferred that each respective pad 14 be aligned with an end edge of the respective panel, such as the forward end edge thereof, the precise placement of each pad 14 on its respective panel can be readily varied through selected operation of the present apparatus, such as by controls 60 which interconnect the pull rolls 44, knife and anvil rolls 46 and 48, and transfer drum 50.

As will be appreciated by those skilled in the art, the precise features of the illustrated embodiment can be varied while keeping with the principles disclosed herein. For example, the tension control provided by the movable dancer roll 40 may alternately be provided by mechanisms for effecting ultrasonic ranging, load cell feedback, or surface drive. While a present embodiment of the present apparatus utilizes electronic servo-drive systems to synchronize the various components, it will be appreciated that such a system could be duplicated using mechanical devices without significantly altering the method itself.

As will be further appreciated, the type of material being handled, i.e., absorbent material typically comprising wood pulp fluff, suggests additional features of the system. For example, the vacuum transfer drum 50 may be further ported to a supply of compressed air for direction through the vacuum chamber for periodic cleaning of the drum. It is presently preferred that all rolls which come in contact with the web of material 38 are at least 4 inches in diameter, and are mounted on low friction oil lubricated bearings. As will be appreciated, the size of the rolls has a direct relationship on the amount of wood pulp fluff that is flung off of the rolls as the web of pad material is guided about the various rolls.

From the foregoing, it will be observed that numerous modifications and variations can be effected without departing from the true spirit and scope of the novel concept of the present invention. It is to be understood that no limitations with respect to the specific apparatus illustrated herein are intended or should be inferred. The disclosure is intended to cover by the appended claims all such modifications as fall within the scope of the claims,

What is claimed is:

1. A method for applying discrete pads of absorbent material to a continuously moving substrate, comprising the steps of
    providing a supply reel having a continuous web of absorbent pad material, and moving said continuous web at a first velocity $V_1$;
    cutting said continuous web of material into discrete absorbent pads each having a length L;
    transferring said discrete pads of said material to said moving substrate by moving each said discrete pad of material at a second velocity $V_2$ equal to or greater than the first velocity $V_1$, and equal to the linear speed of movement of said substrate so that the spacing S between adjacent ones of said discrete pads on said substrate equals $L(V_2/V_1) - L$; and
    cutting said substrate into discrete panels each having a respective one of said discrete pads associated therewith to form discrete absorbent panel assemblies each comprising one of said discrete panels and the respective one of said discrete pads, including selectively varying said transferring and pad cutting steps synchronously with said substrate-cutting step in selectively variable relationship so that each said discrete pad can be selectively variably positioned along the length of the respective discrete panel relative to an end edge of the respective panel with each said discrete pad extending no more than the full length of the associated discrete panel to thereby provide a selected region of each of said absorbent panel assemblies, at which region the respective one of said discrete pads is positioned, with a relatively greater absorptive capacity than the remainder of said absorbent panel assembly.

2. A method for applying discrete pads of material in accordance with claim 1, including
    laterally guiding placement of said discrete pads relative to the centerline of said moving substrate.

3. A method for applying discrete pads of material in accordance with claim 1, wherein
    said step of providing said supply reel having the continuous web of pad material at said first velocity $V_1$ includes driving said supply reel, pulling said continuous web of said pad material from said supply reel at said first velocity $V_1$, sensing the tension of said continuous web as it is pulled from said supply reel, and adjusting the speed at which said supply reel is driven to adjust the tension of said continuous web of pad material.

4. A method for applying discrete pads in accordance with claim 1, including
    aligning each respective pad with said end edge of the respective panel.

5. A method for applying discrete pads of material in accordance with claim 1, wherein
    said transferring step includes applying vacuum to each said discrete pad for effecting movement of each pad at said second velocity $V_2$.

* * * * *